United States Patent [19]

Virnig

[11] Patent Number: 5,032,323

[45] Date of Patent: Jul. 16, 1991

[54] PROCESS FOR ISOMERIZING EPOXIDES TO KETONES

[75] Inventor: Michael J. Virnig, Santa Rosa, Calif.

[73] Assignee: Henkel Research Corporation, Santa Rosa, Calif.

[21] Appl. No.: 500,423

[22] Filed: Mar. 28, 1990

[51] Int. Cl.$^5$ ............................................... C09F 7/08
[52] U.S. Cl. ..................................... 260/405.6; 568/384; 560/174
[58] Field of Search ................ 568/384; 260/405.6; 560/174

[56] References Cited

U.S. PATENT DOCUMENTS

| | | | |
|---|---|---|---|
| 2,799,708 | 7/1957 | Oakley et al. | 260/593 |
| 3,009,959 | 11/1961 | Heath et al. | 260/593 |
| 3,321,515 | 5/1967 | Moore et al. | 260/544 |

FOREIGN PATENT DOCUMENTS

| | | | |
|---|---|---|---|
| 0192298 | 2/1986 | European Pat. Off. | 568/384 |
| 352875 | 10/1972 | U.S.S.R. | 568/384 |

OTHER PUBLICATIONS

Rutzen et al., Chem. Abst., vol. 101, #112757n (1984).
Journal of Catalysis: 63, 364 (1980); 61, 1 (1980); 68, 209 (1981); 68, 252 (1981); 71, 331 (1981); 100, 39 (1986).
J. Chem. Soc., Faraday Trans, 83(8), 2359 (1987).
Journal of Molecular Catalysis, 44, 337 (1988).
J. Chem. Soc., Chem. Comm., 744 (1979).
Acta Chim. Acad. Scient. Hung. Tomous, 76(4), 417 (1973).
React. Kinet. Catal. Lett., 29(2), 1985.
J. Am. Oil Chem. Soc., 42 126 (1965).
Fette Seifen Anstrichmittel #3, 109 (1984).

*Primary Examiner*—James H. Reamer
*Attorney, Agent, or Firm*—Ernest G. Szoke; Wayne C. Jaeschke; John E. Drach

[57] ABSTRACT

Epoxides are isomerized to ketones by contacting the epoxides with a catalyst effective amount of a substantially fully hydrogenated palladium catalyst at a temperature of from about 200° C. to about 300° C. while contacting the epoxides with hydrogen at a partial pressure of equal to or less than one atmosphere.

18 Claims, No Drawings

PROCESS FOR ISOMERIZING EPOXIDES TO KETONES

BACKGROUND OF THE INVENTION

1. Field of the Invention

This invention relates to a process for isomerizing epoxides to ketones.

2. Description of the Related Art

The isomerization of epoxides to ketones is known in the art. U.S. Pat. No. 2,799,708 teaches that epoxides having from 4 to 16 carbon atoms wherein the epoxide group is joined to at least one secondary carbon atom are isomerized to ketones by contacting the epoxide with a metal from groups IB and VIII of the periodic table supported on an activate carbon base at a temperature of from about 200° C. to about 500° C. Hydrogen is not used in the process. U.S. Pat. No. 3,009,959 teaches that epoxides having from 4 to 16 carbon atoms wherein the epoxide group is joined to at least one secondary carbon atom are isomerized to ketones by contacting the epoxide at a temperature of from about 200° C. to about 500° C. and at a pressure of 150-350 psig in the presence of hydrogen at 0.5-6.0 hydrogen-epoxide mole ratio with copper on an activated carbon base. U.S. Pat. No. 3,321,515 teaches a method for making fluorinated ketones by contacting fluorinated epoxides with a catalytic amount of an alkali metal fluoride. European Patent Application 0192298 teaches a method for the gas phase isomerization of a saturated alkene or cycloalkene oxide to the corresponding ketone using a catalyst that contains a noble metal of group VIII in the periodic table deposited on a basic support in the presence of hydrogen.

The mechanism of the gas phase isomerization of epoxides over noble metal catalysts has been reported in J. Catal., 63, 364 (1980), J. Catal., 61, 1 (1980), J. Catal., 68, 209 (1981), J. Catal., 68, 252 (1981), J. Catal., 71, 331 (1981), J. Catal., 100, 39 (1986), J. Chem. Soc., Faraday Trans., 83(8), 2359 (1987), J. Mol. Catal., 44, 337 (1988), J. Chem. Soc., Chem. Comm., 744 (1979), Acta Chim. Acad. Scient. Hung. Tomus, 76(4), 417 (1973), React. Kinet. Catal. Lett., 29(2), (1985)

Liquid phase epoxide-to-ketone isomerizations have been accomplished using various types of acidic catalysts such as $BF_3$-etherate as taught in J. Am. Oil Chem. Soc., 42, 126 (1965) and Fette Seifen Anstrichmittel #3, 109 (1984) teaches that terminal and inner olefin epoxides can be isomerized to the corresponding carbonyl compounds by reaction with acidic catalysts such as HI.

None of the prior art methods discloses isomerization of an epoxide in the liquid phase using a palladium catalyst. None of the prior art methods discloses isomerization of an epoxide having a ester, ketone, or ether functionality in the liquid phase or gas phase using a palladium catalyst at relatively low temperatures and at atmospheric pressure.

SUMMARY OF THE INVENTION

The present invention provides a process for preparing a ketone comprising the steps of: (a) forming a liquid phase reaction mixture comprising an epoxide of the formula I

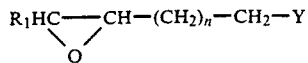

wherein $R_1$ is an aliphatic radical having from 1 to 12 carbon atoms, n is an integer having a value of from 0 to 11, Y is H, $-COOR_2$, $-COR_2$, $-OR_3$, wherein $R_2$ and $R_3$ are each an aliphatic radical having from 1 to 25 carbon atoms, an aryl or substituted aryl group and a catalyst effective amount of a substantially fully hydrogenated palladium catalyst, and (b) contacting said liquid phase reaction mixture with hydrogen having a partial pressure of less than about one atmosphere at a temperature of from about 200° C. to about 300° C. for a period of time sufficient to convert substantially all of the epoxide groups to ketone groups.

The present invention also provides a process for preparing a polyketone comprising the steps of: (a) forming a liquid phase reaction mixture comprising a polyepoxide and a catalyst effective amount of a substantially fully hydrogenated palladium catalyst, and (b) contacting said liquid phase reaction mixture with hydrogen having a partial pressure of less than about one atmosphere at a temperature of from about 200° C. to about 300° C. for a period of time sufficient to convert substantially all of the epoxide groups to ketone groups.

DESCRIPTION OF THE PREFERRED EMBODIMENTS

The present invention provides a general method of preparing a ketone by isomerizing an epoxide in the liquid phase over a substantially fully hydrogenated palladium catalyst while contacting the epoxide with hydrogen whose partial pressure is one atmosphere or less. The process of the present invention is generally carried out by contacting a reaction mixture comprised of an epoxide in the liquid phase and a palladium catalyst heated from about 200° C. to about 300° C. while contacting the reaction mixture with hydrogen whose partial pressure is one atmosphere or less. The reaction mixture is contacted with hydrogen continuously until substantially all of the epoxy compound has disappeared as indicated by analysis of the reaction mixture by gas chromatography. The reaction mixture is then cooled to room temperature and the catalyst is separated from the reaction product usually by filtration. The catalyst can be reused in subsequent reactions.

The liquid phase reaction mixture can be contacted with hydrogen in any convenient manner as long as the partial pressure of the hydrogen is about one atmosphere or less. For example, in the instance where the epoxide has a boiling point above the reaction temperature range (200° C. to about 300° C.), such as epoxidized soybean oil, hydrogen gas can be passed through the reaction mixture by directly introducing it below the liquid level and bubbling it through the liquid. In cases where the boiling point of the epoxide is below the reaction temperature range and the reaction must be carried out in a pressure vessel in order that the epoxide remain a liquid, the reaction mixture can be contacted with hydrogen by pressurizing the vessel to a partial pressure of hydrogen of equal to or less than one atmosphere in admixture with an inert gas.

It is essential that the palladium catalyst be substantially fully hydrogenated in order that reaction occur. For purposes of this invention, a substantially fully hydrogenated catalyst is a catalyst that has been fully saturated with hydrogen. The catalyst may be made substantially fully hydrogenated by dispersing it as received in an inert solvent such as a liquid paraffin and passing gaseous hydrogen through the catalyst-solvent dispersion for about 2 hours at temperatures from room temperature to 200° C. A preferred method of substantially fully hydrogenating the catalyst of the present invention is by taking a 5% palladium-on-carbon catalyst as received from the manufacturer and using it in the process of the present invention. The catalyst is then substantially fully hydrogenated and can be recycled in the process. Any finely divided form of elemental palladium can be used in the process of the present invention. It is preferred that the palladium be deposited on an inert carrier in an amount of from about 1% to about 10% by weight, and more preferred in an amount equal to about 5% by weight of palladium based on the total weight of the palladium/inert carrier weight. For maximum yield of ketone product, it is most preferred that the catalyst be sulfided 5% palladium-on-carbon. Sulfided 5% palladium-on-carbon catalyst is available commercially (sold as palladium on sulfided carbon by Aldrich Chemical Co., Milwaukee, Wisc.). The preferred inert carrier is activated carbon.

The amount of catalyst that is required in the process of the present invention is any amount that is necessary to complete the conversion of epoxide functionality to a ketone in a reasonable period of time such as 3 to 6 hours. The preferred amount of catalyst is in the range of 0.5% to 10% by weight of epoxy compound. The most preferred amount of catalyst is 2.5% by weight of epoxy compound.

Any compound having one or more epoxy groups can be isomerized by the process of the present invention. Examples of such epoxy compounds include but are not limited to propylene oxide (1,2-epoxypropane), butylene oxide (both 1,2-epoxybutane and 2,3-epoxybutane), epoxycyclohexane, and 9,10-epoxyoctadecane. Examples also include epoxy compounds having keto, ester, and ether functionalities, such as epoxidized oils, i.e. epoxidized oleate esters, epoxidized sunflower, soy bean, jojoba and linseed oils. Examples of compounds having more than one epoxide group (a polyepoxide) include but are not limited to epoxidized triglycerides such as epoxidized sunflower, soy bean, jojoba and linseed oils and epoxidized ethers wherein both hydrocarbon radicals have epoxide groups such as epoxidized dioleyl ether, and the like.

The process of the present invention can be carried out at any temperature between 200° C. and 300° C. The most preferred temperature range is from about 250° C. to about 275° C.

In a preferred embodiment of the process of the present invention, an epoxidized triglyceride (having an average of more than one epoxide group per molecule) is mixed with about 2.5% (dry weight) of wet sulfided 5% palladium-on-carbon. The mixture is then heated to about 225° C. for about 2 hours while maintaining a constant flow of hydrogen through the reaction mixture. The progress of the reaction is monitored by GC analysis of the reaction mixture. When no observable epoxidized triglyceride remains, the reaction mixture is cooled to room temperature and the catalyst separated by filtration.

The following examples are meant to illustrate but not limit the invention.

EXAMPLE 1

Isomerization of Epoxidized New Sunflower Oil Using Sulfided 5% Pd/C

Into a 3-neck morton flask equipped with a thermometer, a glass paddle stirrer, a condenser, and a glass frit for gas introduction were placed 50 grams of epoxidized new sunflower oil and 1.25 grams (dry weight) of wet sulfided 5% palladium-on-carbon. The contents of the flask were heated with stirring while maintaining a temperature of about 225° C. for about 2 hours while hydrogen was constantly swept through the flask. The reaction mixture was allowed to stir until GC analysis showed that all of the epoxy acids constituting the epoxidized new sunflower oil had been converted. The reaction mixture was then cooled to room temperature and the catalyst separated by filtration to yield 46-48 grams of a tan, waxy solid. The samples of the final product were either saponified with NaOH and the resultant mixture of fatty acids analyzed by GC analysis of their silyl esters or the final product was transesterified with methanol and the mixture of fatty acid methyl esters was analyzed by GC. The fatty acid distribution of the starting material and the final product are given in Table 1.

TABLE 1

| Fatty Acid Distribution of Starting Material and Final Product[1] | | |
|---|---|---|
| Fatty Acid | Starting Material | Product |
| Palmitic | 4.7 | 5.6 |
| Stearic | 5.8 | 21.5 |
| 9,10-epoxystearic | 76.9 | 0.0 |
| 9(10)-ketostearic | 1.5 | 50.1 |
| Diepoxystearic | 6.7 | 0.0 |
| Diketostearic | 0.0 | 3.6 |

[1]Area % of methyl esters by GLC analysis.

EXAMPLE 2

Isomerization of Epoxidized New Sunflower Oil Using Recycled Catalyst From Example 1.

The procedure of Example 1 was repeated exactly except that the catalyst used was recovered from Example 1. The fatty acid distribution of the final product is given in Table 2.

TABLE 2

| Fatty Acid Distribution of Starting Material and Final Product[1] | | |
|---|---|---|
| Fatty Acid | Starting Material | Product |
| Palmitic | 4.7 | 5.0 |
| Stearic | 5.8 | 15.4 |
| 9,10-epoxystearic | 76.9 | 0.8 |
| 9(10)-ketostearic | 1.5 | 59.3 |
| Diepoxystearic | 6.7 | 0.0 |
| Diketostearic | 0.0 | 1.9 |

[1]Area % of methyl esters by GLC analysis.

EXAMPLE 3

Isomerization of Epoxidized New Sunflower Oil Using Sulfided 5% Pd/C.

The procedure of Example 1 was repeated exactly except that the reaction was run for 3 hours at 275.C. The fatty acid distribution of the final product is given in Table 3.

TABLE 3

Fatty Acid Distribution of Starting Material and Final Product[1]

| Fatty Acid | Starting Material | Product |
| --- | --- | --- |
| Palmitic | 4.7 | 4.5 |
| Stearic | 5.8 | 28.0 |
| 9,10-epoxystearic | 76.9 | 0.0 |
| 9(10)-ketostearic | 1.5 | 43.7 |
| Diepoxystearic | 6.7 | 0.0 |
| Diketostearic | 0.0 | 1.0 |

[1]Area % by GLC analysis.

EXAMPLE 4

Isomerization of Epoxidized New Sunflower Oil Using Recycled Catalyst From Example 3.

The procedure of Example 3 was repeated exactly except that the catalyst used was recovered from Example 3. The fatty acid distribution of the final product is given in Table 4.

TABLE 4

Fatty Acid Distribution of Starting Material and Final Product[1]

| Fatty Acid | Starting Material | Product |
| --- | --- | --- |
| Palmitic | 4.7 | 4.5 |
| Stearic | 5.8 | 16.8 |
| 9,10-epoxystearic | 76.9 | 0.0 |
| 9(10)-ketostearic | 1.5 | 62.7 |
| Diepoxystearic | 6.7 | 0.0 |
| Diketostearic | 0.0 | 4.8 |

[1]Area % by GLC analysis.

EXAMPLE 5

Isomerization of Epoxidized New Sunflower Oil Using 5% Pd/C.

The procedure of Example 1 was repeated exactly except that the reaction was run for 7 hours at 275° C. and the catalyst used was 5% palladium-on-carbon (Pd/C). The fatty acid distribution of the final product is given in Table 5.

TABLE 5

Fatty Acid Distribution of Starting Material and Final Product[1]

| Fatty Acid | Starting Material | Product |
| --- | --- | --- |
| Palmitic | 4.7 | 3.9 |
| Stearic | 5.8 | 14.7 |
| 9,10-epoxystearic | 76.9 | 0.0 |
| 9(10)-ketostearic | 1.5 | 49.4 |
| Diepoxystearic | 6.7 | 0.0 |
| Diketostearic | 0.0 | 1.3 |

[1]Area % by GLC analysis.

EXAMPLE 6

Isomerization of Epoxidized New Sunflower Oil Using Recycled Catalyst From Example 5.

The procedure of Example 5 was repeated exactly except that the catalyst used was recovered from Example 5. The fatty acid distribution of the final product is given in Table 6.

TABLE 6

Fatty Acid Distribution of Starting Material and Final Product[1]

| Fatty Acid | Starting Material | Product |
| --- | --- | --- |
| Palmitic | 4.7 | 5.0 |
| Stearic | 5.8 | 9.6 |
| 9,10-epoxystearic | 76.9 | 0.0 |
| 9(10)-ketostearic | 1.5 | 54.9 |
| Diepoxystearic | 6.7 | 0.0 |
| Diketostearic | 0.0 | 2.8 |

[1]Area % by GLC analysis.

EXAMPLE 7

Isomerization of Epoxidized Soybean Oil Using Sulfided 5% Pd/C

Into a 3-neck morton flask equipped with a thermometer, a glass paddle stirrer, a condenser, and a glass frit for gas introduction were placed 250 grams of epoxidized soybean oil and 6.25 grams (dry weight) of wet sulfided 5% palladium-on-carbon. The contents of the flask were heated with stirring while maintaining a temperature of about 275° C. for about 2 hours while hydrogen was constantly swept through the flask. The reaction mixture was allowed to stir until GC analysis showed that no epoxidized sunflower oil remained. The reaction mixture was then cooled to room temperature and the catalyst separated by filtration. The resulting product (248.8 grams) was saponified and then distilled under vacuum to yield 140.4 grams of a whitish, waxy solid. The samples of the final product were either saponified with NaOH and the resultant mixture of fatty acids analyzed by GC analysis of their silyl esters or the final product was transesterified with methanol and the mixture of fatty acid methyl esters was analyzed by GC. The fatty acid distribution of the final product is given in Table 7.

TABLE 7

Fatty Acid Distribution of Final Product[1]

| Fatty Acid | Product |
| --- | --- |
| Palmitic | 5.6 |
| Unsaturated C-18 | trace |
| Stearic | 10.2 |
| Furanoic Fatty Acids | 6.2 |
| 9,10-epoxystearic | 0.0 |
| 9(10)-ketostearic | 32.4 |
| Diepoxides | 0.0 |
| Mixed keto acids | 23.7 |

[1]Area % by GLC analysis.

EXAMPLE 8

Isomerization of Epoxidized Soybean Oil Using 5% Pd/C.

The procedure of Example 7 was repeated exactly except that the catalyst used was 5% palladium-on-carbon (Pd/C). The fatty acid distribution of the final product is given in Table 8.

TABLE 8

Fatty Acid Distribution of Final Product[1]

| Fatty Acid | Product |
| --- | --- |
| Palmitic | 14 |
| Unsaturated C-18 | 2.5 |
| Stearic | 8.6 |
| Furanoic Fatty Acids | 6.2 |
| 9,10-epoxystearic | 0.0 |
| 9(10)-ketostearic | 32.1 |
| Diepoxides | 0.0 |

TABLE 8-continued

| Fatty Acid Distribution of Final Product[1] | |
|---|---|
| Fatty Acid | Product |
| Mixed keto acids | 25.6 |

EXAMPLE 9

Isomerization of Epoxidized New Sunflower Oil Methyl Esters Using Sulfided 5% Pd/C in a Nitrogen Atmosphere Followed by a Hydrogen Atmosphere Into a 3-neck morton flask equipped with a thermometer, a glass paddle stirrer, a condenser, and a glass frit for gas introduction were placed 200 grams of epoxidized new sunflower oil methyl esters and 5.0 grams of recycled sulfided 5% palladium-on-carbon. The contents of the flask were heated with stirring while maintaining a temperature of about 275° C. for about 3 hours while nitrogen was constantly swept through the flask followed by an additional hour wherein the nitrogen was replaced by hydrogen. GC analysis of the final product showed 89% of the starting 9,10-epoxystearate had been converted to the 9(10)-ketostearate.

COMPARATIVE EXAMPLE 10

Isomerization of Epoxidized New Sunflower Oil Using Recycled Catalyst From Example 5 in a Nitrogen Atmosphere The procedure of Example 5 was repeated exactly except that the catalyst used was recovered from Example 5 and the hydrogen atmosphere was replaced by nitrogen. The fatty acid distribution of the final product is given in Table 10.

TABLE 10

| Fatty Acid Distribution of Starting Material and Final Product[1] | | |
|---|---|---|
| Fatty Acid | Starting Material | Product |
| Palmitic | 4.7 | 4.7 |
| Stearic | 5.8 | 6.4 |
| 9,10-epoxystearic | 76.9 | 52.9 |
| 9(10)-ketostearic | 1.5 | 8.3 |
| Diepoxystearic | 6.7 | 0.0 |
| Diketostearic | 0.0 | 0.0 |

[1]area % by GLC analysis.

EXAMPLE 11

Gas Chromatographic Conditions

All GC analyses were carried out using a 30 m×0.25mm fused silica capillary column having a 0.25 micron thick film of a bonded silicone (SPB-5, Suppelco, Inc., Belafonte, Pa.) using a flame ionization detector operated at 300° C. The helium carrier gas flow rate was about 1.5 ml/min. The column temperature program was one minute at 200° C. followed by heating at a rate of 5° C./min to 250° C. followed by heating at a rate of 20° C./min from 250° C. to 290° C.

EXAMPLE 12

Sample Preparation for GC Analysis

Free acids were analyzed by dissolving 5 microliters of the molten acid in 0.75 ml of TRI-SIL reagent (Pierce Chemical Co., Rockford, Ill.). One microliter of the resultant solution was injected onto the GC column.

The isomerized oil products were either transesterified to the methyl esters or saponified to the free acids before GC analysis.

The saponification was carried out by heating about 3 grams of the isomerized oil and about 5 grams of water to a temperature of about 80° C. while stirring. Then about 1 gram of a 50% by weight aqueous NaOH solution was added and the mixture stirred for 2 hours at 90°–95° C. About 1.22 grams of a 50% by weight aqueous $H_2SO_4$ solution was added slowly while maintaining the temperature below 100° C. to avoid foaming. About 10–15 ml of toluene is then added and stirred and the phases allowed to split. The organic phase is then washed to neutrality with water and the toluene is removed in vacuo to give the free acids.

The transesterification was carried out by refluxing about 2 grams of the isomerized oil with 30 mg of sodium methoxide in 10–15 ml of methanol for about 2 hours. The reaction mixture was then poured into 30 ml of toluene and 30 ml of water containing 3 drops of concentrated HCl. The resulting mixture was then shaken together and the phases allowed to separate. The toluene phase was separated, filtered, and the toluene removed by reduced pressure distillation. About 5 microliters of the resultant esters is then dissolved in 1 ml of toluene and a 1 microliter sample of this solution was injected onto the GC column.

What is claimed is:

1. A process for preparing a ketone comprising the steps of: (a) forming a liquid phase reaction mixture comprising an epoxide of the formula I

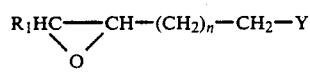

wherein $R_1$ is an aliphatic radical having from 1 to 12 carbon atoms, n is an integer having a value of from 0 to 11, Y is H, $-COOR_2$, $-COR_2$, $-OR_3$, wherein $R_2$ and $R_3$ are each an aliphatic radical having from 1 to 25 carbon atoms, an aryl or substituted aryl group and a catalyst effective amount of a substantially fully hydrogenated palladium catalyst, and (b) contacting said liquid phase reaction mixture with hydrogen having a partial pressure of less than about one atmosphere at a temperature of from about 200° C. to about 300° C. for a period of time sufficient to convert substantially all of the epoxide groups to ketone groups.

2. The process of claim 1 wherein said catalyst is palladium-on-carbon or sulfided palladium-on-carbon.

3. The process of claim 2 wherein the amount of palladium in said catalyst is from about 1% to about 10% by weight.

4. The process of claim 1 wherein said catalyst is 5% palladium-on-carbon.

5. The process of claim 1 wherein said catalyst is 5% sulfided palladium-on-carbon.

6. The process of claim 2 wherein the amount of said catalyst is equal to from about 0.5% to about 10% by weight of said epoxide of formula I.

7. The process of claim 4 wherein the amount of said catalyst is equal to about 2.5% by weight of said epoxide of formula I.

8. The process of claim 1 wherein said epoxide of formula I is epoxidized new sunflower oil methyl esters.

9. A process for preparing a polyketone comprising the steps of: (a) forming a liquid phase reaction mixture comprising a polyepoxide and a catalyst effective amount of a substantially fully hydrogenated palladium catalyst, and (b) contacting said liquid phase reaction mixture with hydrogen having a partial pressure of less than about one atmosphere at a temperature of from about 200° C. to about 300° C. for a period of time sufficient to convert substantially all of the epoxide groups to ketone groups.

10. The process of claim 9 wherein said catalyst is palladium-on-carbon or sulfided palladium-on-carbon.

11. The process of claim 10 wherein the amount of palladium in said catalyst is from about 1% to about 10% by weight.

12. The process of claim 9 wherein said catalyst is 5% palladium-on-carbon.

13. The process of claim 9 wherein said catalyst is 5% sulfided palladium-on-carbon.

14. The process of claim 9 wherein the amount of said catalyst is equal to from about 0.5% to about 10% by weight of said polyepoxide.

15. The process of claim 14 wherein the amount of said catalyst is equal to about 2.5% by weight of said polyepoxide.

16. The process of claim 9 wherein said polyepoxide is an epoxidized triglyceride.

17. The process of claim 16 wherein said polyepoxide is epoxidized new sunflower oil.

18. The process of claim 16 wherein said polyepoxide is epoxidized soybean oil.

* * * * *